United States Patent [19]

Monks

[11] 4,388,241
[45] Jun. 14, 1983

[54] BILE ACIDS

[75] Inventor: Reginald Monks, Amersham, England

[73] Assignee: The Radiochemical Centre Limited, Buckinghamshire, England

[21] Appl. No.: 224,922

[22] Filed: Jan. 14, 1981

Related U.S. Application Data

[63] Continuation of Ser. No. 54,574, Jul. 3, 1979, abandoned.

[30] Foreign Application Priority Data

Jul. 3, 1978 [GB] United Kingdom ............... 28569/78

[51] Int. Cl.$^3$ ................................................ C07J 9/00
[52] U.S. Cl. ................................................ 260/397.1
[58] Field of Search ...................................... 260/397.1

[56] References Cited

U.S. PATENT DOCUMENTS 4,104,285  8/1978  Torres et al. ...................... 260/397.1
4,172,085  10/1979 Monks et al. ..................... 260/397.1

OTHER PUBLICATIONS

Delhez et al., "European Journal Nuclear Medicine", (1982), No. 7, pp. 269-271.

Primary Examiner—Elbert L. Roberts
Attorney, Agent, or Firm—Wenderoth, Lind & Ponack

[57] ABSTRACT

Novel compounds having the formula (II)

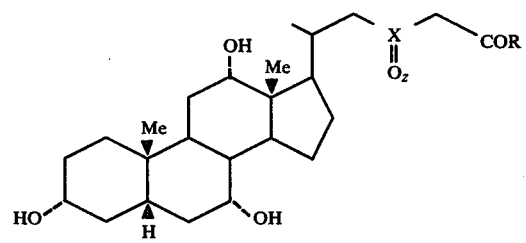

where X is radioactive Se or Te, z is 0 or 1 and R is OH or an amino acid residue, particularly 23-[$^{75}$Se]-selena-25-homocholic acid and its glycine and taurine conjugate have outstandingly good properties for the investigation of bowel function.

8 Claims, No Drawings

BILE ACIDS

This application is a continuation application of Ser. No. 54,574, filed July 3, 1979, now abondoned.

This invention relates to selenium and tellurium derivatives, particularly γ-emitting radioactive derivatives, of bile acids and bile salts. Such compounds are valuable in the examination of body function, especially small bowel function.

Bile salts are synthesized in the liver from cholesterol, pass via the hepatic and common bile ducts to the intestinal tract, are absorbed in the ileum and return to the liver via the portal venous system. During the enterohepatic circulation in a normal human more than 95 per cent of the bile salts entering the small intestine are reabsorbed, the remainder entering the large intestine and eventually appearing in the faeces. Malfunctioning of the ileum, which can be caused by a number of pathological conditions, can result in the deficient absorption of bile salts. A measurement of bile salt absorption by the intestine would therefore provide useful information enabling the distal small bowel to be recognised, or eliminated, as the source of gastrointestinal disorder.

Bile acids may be represented by the following formula:

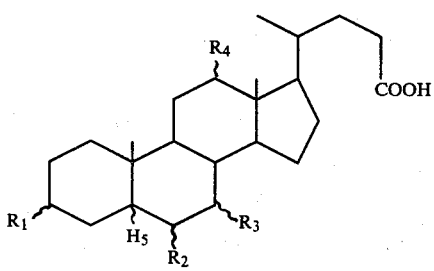

(1)

wherein $R_1$, $R_2$, $R_3$ and $R_4$ are, independently a hydrogen atom or an α- or β-hydroxy group, and wherein $H_5$ is either in the α or β position.

Bile salts are conjugates of the above bile acids with amino acids, in particular glycine and tourine.

Carboxyl-$^{14}$C-cholic acid (1, $R_2=H$, $R_1=R_3=R_4=$α-CH; $H_5$ is β) and its tourine conjugate have been used to study the absorption of bile salts in the intestine of both animals and man under a variety of pathological conditions, e.g. regional ileitis, ileal resection, and induced diarrhoea. The investigations have required the measurement of $^{14}$C radioactivity in faeces, urine and bile. In the breath test as devised by Fromm and Hofmann glycine-1-[$^{14}$C] glycocholate is used to detect increased bacterial deconjugation of the bile salts. Upon deconjugation in the small bowel as a result of bacterial overgrowth or in the colon following bile salt malabsorption, the glycine liberated is metabolized, absorbed, and partly exhaled as $^{14}CO_2$. In the case of bile salt malabsorption some of the $^{14}$C radioactivity will appear in the faeces. A faecal $^{14}$C measurement is essential for complete exploitation of the diagnostic scope of the breath test. In the diagnosis of bile acid malabsorption the Schilling test employing labelled cyano-cobalamin with intrinsic factor is often helpful, but by itself it cannot discriminate between bacterial overgrowth and ileal dysfunction.

Our co-pending British Patent applications 628/77 and 632/78 (corresponding to German DOS 2800781.0 and 2800780.9) relate to selenium and tellurium derivatives of bile acids and bile salts and to their use in investigating body function, particularly small bowel function.

The present invention relates to certain selenium and tellurium derivatives of homocholic acid which have proved to have outstandingly and unexpectedly good properties for this purpose.

The invention provides compounds having the formula (II):

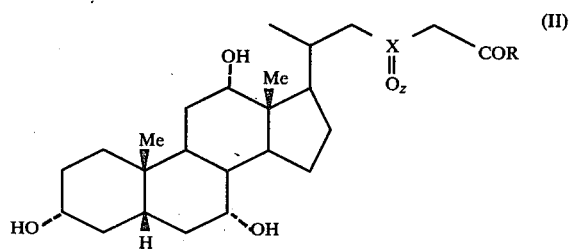

where
X is Se or Te,
z is 0 or 1, and
R is OH or a radical derived by removal of a hydrogen atom from the amino group of an amino acid.

Preferably X is Se, z is 0 and R is OH or the radical derived from glycin or taurine. The invention includes the non-radioactive compounds and also the compounds labelled with radioactive isotopes of selenium and tellurium e.g. selenium-75 and Tellurium-123m. The non-radioactive compounds are useful aids in determining the properties of the radioactive compounds.

Preparation of the compounds is described in the Examples which follow. The tellurium derivatives may be prepared by methods previously disclosed in our German DOS 28 00 781.0 and 28 00 780.9.

The following uses are envisaged for the radioactive derivatives of this innvention:

(i) To detect malfunctioning of the enterohepatic circulation or any part thereof, e.g. intestine, liver or gall bladder, by either measurement of body or tissue radioactivity or by visualization of a particular organ following either oral or intravenous administration of the labellel seleno- or telluro- bile acid. This use includes the study of small bowel absorption and liver function.

(ii) To visualize and quantify bile reflux from the duodenum into the stomach in relation to the study of gastritis.

(iii) To measure the total circulating bile acid pool by an isotopic dilution method employing a labelled seleno bile acid. This information can be of value in the assessment of dose, in the dissolution of cholesterol gallstones with chenodeoxycholic acid.

The radioactive derivatives of this invention may conveniently be formulated: for oral administration—solution or capsule; for intravenous administration—sterile solution in water or isotonic saline or water/alcohol mixture.

EXAMPLE 1

The preparation of 3α, 7α, 12α-trihydroxy-22-(carboxymethyl-[$^{75}$Se]seleno)-23,24-bis nor-5β-cholane (23-Selena-25-homocholic acid-$^{75}$Se)

(1) 3α, 7α, 12α-Triacetoxy-22-iodo-23,24-bis nor 5β-cholane

3α, 7α, 12α-Triacetoxy-24-nor-5β-cholanic acid (4.1 g—prepared from methyl cholate by Barbier-Wieland degradation, see e.g. Organic Synthesis, Vol. 24, 38–43; T. Shimizu and T. Kazuno, Z. physical Chem. 244, 167 (1936) in dry carbon tetrachloride (150 ml.) was treated with dry, powdered, lead tetracetate (4.1 g) and was heated to reflux in an atmosphere of dry nitrogen. The solution was irradiated with an Atlas 275 watt infra-red lamp and a solution of iodine (2.25 g) in dry carbon tetrachloride (100 ml.) was added portion-wise over a period of 15 minutes. The reaction mixture was irradiated and stirred for a further 1 hour and was allowed to cool. The solution was filtered, the filtrate was washed successively with 5% sodium thiosulphate solution and water, and was dried over anhydrous sodium sulphate. Evaporation of the solvent left an oil which was dissolved in ethyl acetate/hexane (⅓). The solution was loaded on a column prepared from Merck Silica Gel 60 (70-230 mesh) (150 g) and the product was isolated by elution with ethyl acetate/hexane (⅓). The fractions containing the product were pooled and evaporated under reduced pressure giving 3α, 7α, 12α-triacetoxy-22-iodo-23,24-bis nor-5β-cholane (1.9 g) as a solid foam which could not by crystallised.

TLC (Merck Kieselgel 60 F$_{254}$; chloroform)
Single Component Rf 0.80.

IR Spectrum
$\bar{v}$max: 2940, 2870, 1737, 1450, 1380, 1368, 1245, 1023 cm$^{-1}$.

NMR Spectrum (220 MH$_2$, CDCl$_3$)
τ 4.93 (IH,S,C$_{12}$-proton); τ 5.07 (IH,S,C$_7$-proton);
τ 5.40 (IH,m,C$_3$-proton); τ 6.73 (2H,m,C$_{22}$-protons);
τ 7.87–τ 7.94 (9H,3S,3-,7-ono 12-acetate protons); τ 9.07 (6H,S (with minor splitting ), C$_{19}$-protons+C$_{21}$-protons); τ 9.22 (3H,S,C$_{18}$-protons).

(ii) 23-Selena-25-homocholic acid-$^{75}$Se

Red Selenium-$^{75}$Se was precipitated by bubbling sulphur dioxide through a solution of sodium selenite (17 mg) in water (2 ml) and concentrated hydrochloric acid (4 ml) containing sodium selenite-$^{75}$Se (10.4 m Ci, 1.0 mg selenium). The precipitate was centrifuged off, it was washed thoroughly with de-ionised water and dried over phosphorus pentoxide under vacuum. Red selenium-$^{75}$Se (7.4 mg, 0.094 mA, 8.8 m Ci) was suspended in ethanol (2 ml) and potassium cyanide (6.2 mg, 0.095 m mole) was added; the mixture was stirred at room temperature for two hours when complete solution had occurred. Ethyl bromoacetate (10.5 μl) was added to the solution at 0° C. and it was stirred for 1½ hours.

3α, 7α, 12α-Triacetoxy-22-iodo-23,24-bis-5β-cholane (57 mg, 0.095 m mole) in ethanol (1 ml) was added to sodium borohydride (9 mg) in ethanol (1 ml). The reaction mixture was cooled in ice and the ethanolic solution of ethyl selenocyanatoacetate-$^{75}$Se was added over a period of 10 minutes. Stirring was continued for a further 2 hours while the temperature rose to room temperature. Acetone (1 ml) was added and the solution was evaporated under reduced pressure. Chloroform (2 ml) was added to the residue, insoluble material was removed by filtration and the solution was concentrated to a small bulk. The product was isolated by preparative layer chromotography (Anachem Silica Gel GF, 1 mm; ethyl acetate, hexane 1:2). The major radioactive component, Rf 0.36, as located by autoradiography, was removed from the plate and extracted into ethyl acetate (3×4 ml). Yield of ethyl 3α, 7α, 12α-triacetoxy-23-selena-25-homo-5β-cholanate-$^{75}$Se, 5.1 m Ci.

IR Spectrum
$\bar{v}$max: 2935, 2860, 1736, 1460, 1440, 1374, 1362, 1245, 1103, 1023 Cm$^{-1}$.

The solution was evaporated and sodium hydroxide (200 mg) in ethanol (5 ml) and water (2 ml) was added. The solution was stirred and heated under reflux for 2½ hours and was allowed to stand at ambient temperature for 16 hours. The solvent was evaporated under reduced pressure, the residue was dissolved in water (2 ml); and the solution was acidified by the addition of concentrated hydrochloric acid. The solvent was removed under reduced pressure, the residue was dissolved in a little methanol and the product was isolated by preparative layer chromatography (Anachem Silica Gel GF, 1 mm; chloroform, methanol 3:1).

The required band, Rf 0.33, was located by autoradiography; it was removed from the plate and the product was isolated by extraction into methanol. Evaporation of the solvent afforded 23-selena-25-homocholic acid-$^{75}$Se (3.0 m Ci, 34%).

TLC Merck Kieselgel 60 F$_{254}$)
(a) Chloroform, methanol—3:1, Major Component (93%) Rf 0.42.
(b) Dichloromethane, Acetone, Acetic Acid—7:2:1.5; Major Component (97%) Rf 0.76.

IR Spectrum
$\bar{v}$ max: 3400, 2920, 2860, 1708, 1380, 1263, 1104, 1025 cm$^{-1}$.

(iii) Ethyl 3α, 7α, 12α-Triacetoxy-23-Selena-25-homo-5β-cholanate and 23-Selena-25-homocholic acid Non-radioactive ethyl 3α, 7α, 12α-triacetoxy-23-selena-25-homo-5β-cholanate and 23-selena-25-homocholic acid were prepared by the method described in 1(ii).

Quantities of reagents used:
ethyl selenocyanatoacetate (105 mg) in 1.5 ml ethanol; sodium borohydride (36 mg); 3α, 7α, 12α-triacetoxy-22-iodo-23,24-bis nor 5β-cholane (305 mg); ethanol (10 ml). Yield of ethyl 3α, 7α, 12α-triacetoxy-23-selena-25-homo-5β-cholanate, 215 mg.

Crude ethyl 3α. 7α. 12α-triacetoxy-23-selena-25-homo-5β-cholanate (ca. 1.4 g) was purified by column chromatography on Merck Kieselgel 60 (70-230 mesh) with ethylacetate; hexane - 2:5 as eluent. A portion of the purified product was recrystallised twice from hexane containing a few drops of benzene to give a fine crystalline product m.p. 118°–119° C.

Elemental Analysis: Found: 59.9%C, 7.72%H, 19.85%O C$_{32}$H$_{50}$O$_8$Se requires: 59.89%C, 7.85%H, 19.95%O.

IR Spectrum
$\bar{v}$ max: 2940, 2865, 1738, 1470, 1445, 1380, 1368, 1250, 1025 cm$^{-1}$.

NMR (220 MH$_2$, CDCl$_3$)
τ 4.90 (IH,S,C$_{12}$-proton); τ5.06 (IH,S,C$_7$-proton); τ 5.39 (IH,m,C$_3$-proton); τ 5.81 (2H,q, ethyl CH$_2$); τ 6.87

(2H,S,C$_{24}$-protons); τ7.04 and τ7.38 ((2H, 2q,C$_{22}$-protons), τ7.83, τ7,88, τ7.94 (9H,3S,3-, 7- and 12-acetate protons); τ8.72 (3H,t,ethyl CH$_3$); τ 9.02 (3H,d,C$_{21}$-protons); τ 9.08 (3H,S, C$_{19}$-protons); τ9.24 (3H,S,C$_{18}$-protons).

Ethyl 3α, 7α, 12α-triacetoxy-23-selena-25-homo-5β-cholanate (215 mg) was hydrolysed as described in 1(ii). The product was purified by preparative layer chromatography (two Anachem Silica plates, 1 mm; dichloromethane, acetone, acetic acid 7:2:1.5. The required band was removed from the plate and the product was extracted into methanol. Evaporation of the solvent gave 23-selena-25-homocholic acid (105 mg).

TLC (Merck Kiesegel 60 F$_{254}$)

(a) Chloroform, methanol—4:1, Single component, Rf 0.31, corresponding to 23-selena-25-homocholic acid-$^{75}$Se.

(b) Ethylacetate, hexane, acetic acid—10:5:4; single component, Rf 0.3, corresponding to 23-selena-25-homocholic acid-$^{75}$Se.

IR Spectrum $\bar{\nu}$ max: 3430, 2925, 2855, 1700, 1374, 1255, 1072, 1038, 910, 852 cm$^{-1}$.

NMR Spectrum (220 MH$_2$,C$_5$D$_5$N)

τ1.26, τ2.40, τ2.77 (solvent peaks); τ5.76 (IH,S,C$_{12}$-proton); τ5.90 (IH,S,C$_7$-proton); τ6.23 (IH,m,C$_3$-proton); τ6.49 (2H,S,C$_{24}$-protons); τ8.58 (3H,d,C$_{21}$-protons); τ9.00 (3H,S,C$_{19}$-protons); τ9.19 (3H,S,C$_{18}$-protons).

(iv) Tauro-23-selena-25-homocholic acid-$^{75}$Se

A solution of 23-selena-25-homocholic acid-$^{75}$Se (0.97 m Ci, 9.2μ mole) in methanol was evaporated to dryness. Dry dimethylformamide (200 μl) and N-ethoxycarbonyl-2-ethoxy dihydroquinoline (3.6 mg) were added and the solution was stirred at ambient temperature for 15 minutes. Taurine (1.3 mg) was treated with dimethylformamide (90 μl) containing dry triethylamine (1.8 μl) and stirred at ambient temperature for 15 minutes. The solution of the selenated bile acid was added to the taurine, 2×100 μl of dry dimethylformamide were used to complete the transfer and the reaction mixture was stirred at 90°–95° for 30 minutes. The solvent was evaporated under reduced pressure, methanol was added to the residue, the solution was filtered, acidified by the addition of concentrated hydrochloric acid and evaporated. The product was purified by preparative layer chromatography (Anachem Silica Gel GF, 1 mm, chloroform, methanol 2:1). The required band was located by autoradiography (Rf 0.3), it was removed from the plate and the product was extracted into methanol. Yield of tauro-23-selena-25-homocholic acid 0.64 m Ci.

TLC (Merck Kieselgel 60 F$_{254}$)

(a) n-butanol, water, acetic acid - 60:25:15; Major Component (96%) Rf 0.53 (cf. 23-selena-25-homocholic acid Rf 0.88).

(b) dichloromethane, acetone, acetic acid - 7:2:2; Major component Rf 0.05 (cf 23-selena-25-homocholic acid Rf 0.93)

IR Spectrum $\bar{\nu}$ max: 3430, 2940, 2870, 1638, 1545, 1450, 1387, 1210, 1045

(v) Tauro-23-selena-25-homocholic acid

Taurine (28.4 mg) was dissolved in the minimum of deionised water and the solution was lyophilized. Dry dimethylformamide (490 μl) containing triethylamine (37 μl) was added to the taurine and the slurry was stirred for 20 minutes. 23-Selena-25-homocholic acid (100 mg) was dissolved in dry dimethylformamide (1.1 ml), N-ethoxycarbonyl-2-ethoxydihydroquinol (71.1 mg) was added, and after standing at ambient temperature for 15 minutes the solution was transferred to the flask containing taurine. A further quantity of dry dimethylformamide (200 μl) was used to wash flask and complete the transfer. The reaction mixture was stirred at 90°–95° C. for 30 minutes and for a further 20 minutes while cooling. Solvent was evaporated in vacuo and the residue was dissolved in methanol (5 ml). The solution was acidified by the dropwise addition of concentrated hydrochloric acid and allowed to stand overnight. After evaporation of solvent the residue was dissolved in the minumum volume of methanol and the solvent was applied to an Anachem 1 mm Silica gel preparative TLC plate which was developed in chloroform, methanol - 2. The required band was located under UV light, it was removed from the plate and the product was extracted into methanol. The methanolic solution was evaporated to dryness, chloroform (12 ml) and methanol (3) were added, the solution was filtered to remove silica particles and evaporated to dryness. Finally, the residue was dissolved in water and the solution was filtered through a Millipore Millex 0.45 μm filter and lyophilized to yield tauro-23-selena-25-homocholic acid (78 mg) as a white powder.

IR Spectrum $\bar{\nu}$ max: 3410, 2910, 2845, 1645, 1535, 1450, 1372, 1190, 1072, 1044, 976, 909 cm$^{-1}$.

NMR Spectrum (220 MHz, D$_2$O):

τ5.97 (1H, S, 12β-H), τ6.09 (1H, S, 7β-H), τ6.38 (2H, t, —CH$_2$SO$_3$H), τ6.49 (1H, broad S, 3β-H), τ6.74 (2H, S C$_{24}$H), τ6.87 (2H, t, —CH$_2$CH$_2$SO$_3$H), τ7.06 and 7.38 (2H, d+t, C$_{22}$H), τ8.87 (3H, d, C$_{21}$ H), τ9.09 (3H, S, C$_{19}$H), τ9.29 (3H, S, C$_{18}$H).

EXAMPLE 2

Preparation of Glyco-23-selena-25-homocholic acid (i) Ethyl-23-selena-25-homocholylglycinate Ethyl glycinate hydrochloride (19.5 mg, 0.14 mmole) was suspended in dry ethyl acetate (1 ml) and triethylamine (19.8 μl) was added. The suspension was stirred for 30 minutes. 23-Selena-25-homocholic acid (48.2 mg, 0.10 mmole) was dissolved in dry ethylacetate (3 ml) and N-ethoxycarbonyl-2-ethoxydihydroquinoline (34.2 mg, 0.14 mmole) was added. After stirring for 10 minutes at ambient temperature the solution was transferred to the flask containing ethyl glycinate and the reaction mixture was stirred and heated under reflux on a water bath for 6½ hours. After standing overnight, the reaction mixture was transferred to a separating funnel, ethyl acetate (10 ml) and water (10 ml) were added and the phases were separated. The aqueous phase was extracted once with ethyl acetate (5 ml), and the combined ethyl acetate extracts were washed successively with 0.5 M sodium hydroxide solution (10 ml), water (10 ml), 0.5 M hydrochloric acid solution (2×10 ml) and finally with water (2×10 ml), and then dried over anhydrous sodium sulphate. Evaporation of the solvent left a residue of ethyl 23-selena-25-homocholylglycinate (40 mg). TLC (Merck Kieselgel 60 F$_{254}$; chloroform, methanol 10/1)—Product Rf0.53, cf 23-selena-25-homocholic acid, Rf 0.03.

IR Spectrum

ν max—3380, 2935, 2865, 1740, 1655, 1530, 1470, 1380, 1206, 1080, 1030 cm$^{-1}$.

(ii) Glyco-23-selena-25-homocholic acid

Ethyl 23-selena-25-homocholylglycinate (40 mg) in ethanol (2 ml) in ethanol (2 ml) was heated under reflux on a hot water bath and 10% aqueous potassium carbonate solution (2 ml) was added. After 15 minutes the solution was cooled and solvents evaporated under reduced pressure. The residue was dissolved in water (3 ml) and the solution was acidified by the addition of 0.5 M hydrochloric acid solution. The precipitate was isolated by centrifugation, washed once with 0.5 M hydrochloric acid solution, and dried in vacuo to yield glyco-23-selena-25-homocholic acid (25.4 mg).

TLC (Merck Kieselgel 60 F$_{254}$)

(i) n-butanol, water, acetic acid - 60:25:15:-glyco-23-selena-25-homocholic acid Rf 0.76; cf. 23-selena-25-homocholic acid Rf 0.88 and glycocholic acid Rf 0.69.

(ii) dichloromethane, acetone, acetic acid - 7:5:5:- glyco-23-selena-25-homocholic acid Rf 0.70; cf. 23-selena-25-homocholic acid Rf 0. and glycocholic acid Rf 0.46.

NMR Spectrum; (220 MHz, D$_2$O containing N$_a$OD)

$\tau$5.97(1H, S, 12$\beta$H), $\tau$6.09 (1H,S,7$\beta$H), $\tau$6.22(2H,S,NH CH$_2$CO$_2$H), $\tau$6.51(1H, broad S, 3$\beta$H), $\tau$6.83 (1H,S,C$_{24}$H), $\tau$7.04 and $\tau$7.34 (2H,m,C$_{22}$H),$\tau$8.86 (3H,S,C$_{21}$H),$\tau$9.09 (3H,S,C$_{19}$H),$\tau$9.28(3H,S C$_{18}$H).

EXAMPLE 3

Preparation of Glyco-23-selena-25-homocholic acid - $^{75}$Se

The synthesis was carried out as described for the non-radioactive material using ethyl glycinate hydrochloride (1.3 mg, 9.3 $\mu$mol), ethyl acetate (70 $\mu$l), triethylamine (1.35 $\mu$l), 23-[$^{75}$Se]selena-25-homocholic acid (1.06 mCi, 6.6$\mu$ mol) EEDQ (2.3 mg) and ethyl acetate (200 $\mu$l). After heating under reflux for 6 hrs. the reaction mixture was allowed to stand at ambient temperature for 88 hours. The reaction mixture was treated as described previously, giving a solution of ethyl 23-selena-25-homocholylglycinate-$^{75}$Se (4.26$\mu$ Ci) in ethyl acetate. After removal of solvent the product was hydrolysed with 10% potassium carbonate solution (2 ml) in ethanol (2 ml). The solution was evaporated to dryness and the residue was dissolved in water; the aqueous solution was acidified with 0.5 M hydrochloric acid solution and lyophilized. The residue was extracted with acetone (4 ml) and the solution was filtered from insoluble inorganic salts and concentrated to a small bulk. It was applied to a Merck-Kieselgel 60 F$_{254}$ 2 mm plate which was developed in dichloromethane, acetone acetic acid - 7:5:5. The main radioactive band was located by autoradiography and the product was isolated by washing from the silica with acetone, acetic acid - 2:1. After evaporation of solvents the residue was dissolved acetone (5 ml) and the solution filtered. Yield of glyco-23-selena-25-homocholic acid-$^{75}$Se, 120$\mu$ Ci.

TLC (Merck Kieselgel 60 F$_{254}$)

(i) dichloromethane; acetone; acetic acid - 7:5:5 showed a single component Rf 0.74, corresponding to the non radioactive standard; cf glycocholic acid, Rf 0.47, and 23-selena-25-homocholic acid, Rf 0.89, in the same system.

(ii) n-butanol, acetic acid, water - 60:15:25 showed a single component, Rf 0.78, corresponding to the non radioactive standard; of glycocholic acid, Rf 0.70, and 23-selena-25-homocholic acid, Rf 0.88, in the same system,

EXAMPLE 4

Preparation of Tauro-23-[$^{75}$Se]Selena-25-homocholic acid selenoxide

Tauro-23-[$^{75}$Se]selena-25-homocholic acid (480$\mu$ Ci, 8$\mu$ mole) in methanol (1.5 ml) was treated with an aliquot (40$\mu$ l) of a solution prepared from 29% w/v hydrogen peroxide solution (100$\mu$ l) and deionised water (900$\mu$ l) and the reaction mixture was allowed to stand at ambient temperature overnight. Analytical TLC (Merck Kieselgel 60 F$_{254}$) demonstrated the formation of the product.

n-butanol, water, acetic acid—60:25:15—Selenoxide Rf 0.74, Selenide Rf 0.55 chloroform, methanol, acetic acid, water—65:20:10-:5—Selenoxide Rf 0.88, selenide Rf 0.41 chloroform, methanol—2:1—Selenoxide Rf 0.28, Selenide Rf 0.40

Dichloromethane, acetone, acetic acid—7:5-:5—Selenoxide Rf 0.21, selenide Rf 0.08.

The solution was concentrated to a small bulk and the product was isolated by preparative thin layer chromatography (Anachem 1 mm silica gel—dichloromethane:acetone:acetic acid—1:1:1). The required band was located by autoradiography; it was removed from the plate and the product (160$\mu$ Ci) was isolated by washing the silica with methanol.

BIOLOGICAL EVALUATION (A) Tissue Distribution Studies

Tissue distribution studies in rats, 10 days after oral administration of 23-[$^{75}$Se]selena-25-homocholic acid and its taurine conjugate, show that these two compounds are excreted in the faeces to an extent greater than 95 percent and that the body retention is 2.5 percent or less.

(B) Whole-Body Excretion Studies

Approximately 10–15$\mu$ Ci each of 23-[$^{75}$Se]selena-25-homocholic acid and its taurine conjugate were administered to rats via an intragastric tube. Whole body counts were determined immediately by means of a small whole body counter, and the measurements were repeated at intervals over the following 10 days. A whole body standard permitted corrections for radioactive decay and variations in counter efficiency. Semilogarithmic plots were made of retention of activity against time.

In the case of 23-[$^{75}$Se]selena-25-homocholic acid the graph indicated a major component, greater than 98 percent, for which the time for excretion of half the activity was 1.2 days. For tauro-23-[$^{75}$Se]selena-25-homocholic acid a linear plot was obtained indicating a single component of which half the activity was excreted in 1.8 days, a result which agrees closely with that reported in the literature for $^{14}$C-labelled bile acids. Of the seleno acids tauro-23-[$^{75}$Se]selena-25-homocholic acid most closely resembles the natural bile acids in its pattern of excretion in rats.

(C) Biliary Excretion

A mixture of [$^{14}$C]-cholic acid with either 23-[$^{75}$Se]-selena-25-homocholic acid or its taurine conjugate was administered orally to bile fistula rats and bile was collected quantitatively for a period of 24 hours. $^{14}$C and 75Se radioactivity was measured in both the administered labelled bile acids and in the collected sample of bile, so that the ratio $$\frac{^{14}C/^{75}Se \text{ collected}}{^{14}C/^{75}Se \text{ administered}}$$

could be calculated. For 23-[75Se]selena-25-homocholic acid this ratio was 0.85 and for its taurine conjugate the ratio was 1.23. These figures indicate that the efficiency of intestinal absorption for these two seleno bile acids is closely similar to that for cholic acid and better than that for the compounds disclosed in British Patent Application Nos. 628/77 and 632/78.

The biliary excretion in rats after the intravenous administration of 23-[75Se]selena-25-homocholic acid and its taurine conjugate has also been studied. Both compounds were rapidly and almost completely excreted in the bile, the excretion characteristics for tauro-23-[75Se]selena-25-homocholic acid indicating it to be an excellent liver function agent; the maximum concentration in the bile in terms of % dose/g bile was higher than for 99mTc-E-HIDA (1500% as against 600%), and 99.3% of the dose was excreted into the bile within two hours.

(D) Stability to Intestinal Bacteria

Transport of bile acids through the intestine can take place by both passive diffusion and active transport. The passive diffusion process takes place along the whole length of the intestine whereas active transport, the major process, is confined to the ileum and more so to the distal ileum. The component due to passive non-ionic diffusion can be appreciable and is dependent upon the pKas of the bile acids, which for taurine conjugates is approximately 2 and for free bile acids is approximately 6. At the pH existing in the intestinal lumen, free bile acids are absorbed readily by this passive process but taurine conjugates negligibly so. Obviously, in order to maintain specificity of the taurine conjugates for active transport through the ileum, stability towards deconjugation by gut bacteria is an important factor. The rates of hydrolysis of both [14C]taurocholic acid and tauro-23-[75Se]selena-25-homocholic acid by cholylglycine hydrolase (derived from Clostridium Perfringens), have been compared by incubating both compounds with the enzyme under identical reaction conditions. Whereas [14C] taurocholic acid underwent greater than 50 percent deconjugation within 2 hours, only 8 percent deconjugation of tauro-23-[75Se]selena-25-homocholic acid occurred within 24 hours, with no further conversion evident up to 43 hours. This particular seleno bile acid is thus very much more resistant towards enzymatic deconjugation than is the natural bile acid conjugate.

(E) Clinical Evaluation

1. A mixture of [14C] cholic acid and tauro-23-[75Se]-selena-25-homocholic acid was administered orally to two patients fitted with T-tubes following cholecystectomy, thus allowing direct sampling of their bile and measurement of the ratio $$\frac{^{14}C/^{75}Se \text{ collected in bile}}{^{14}C/^{75}Se \text{ administered}}$$

The values obtained for this ratio, 1.2 and 1.07, are very similar to the value obtained for this ratio in rats, and indicate that in humans this seleno bile acid is absorbed from the gut, transported to the liver and excreted into the bile with the same overall efficiency as the natural bile acid.

The excretion of tauro-23-[75Se]selena-25-homocholic acid has been studied in ten normal humans, following the oral administration of approximately 10μ Ci, by measuring body radioactivity in a whole-body counter immediately after administration and subsequently at intervals over a period of 50 days. The range of values for the times of excretion of 50 percent of this seleno bile acid (2.6–7.2 days) are similar to those reported for [14C] taurocholic and [14C] cholic acids in the literature. It is evident that in humans, as in rats, tauro-23-[75Se]selena-25-homocholic acid is absorbed from the small intestine and incorporated into the enterohepatic circulation in a manner very similar to that applying to natural bile salts. Approximately 10μ Ci of tauro-23-[75Se]selena-25-homocholic acid was given orally to a patient who had undergone a total ileal resection. (This patient was the one who was cited as patient (3) in British Patent Application No. 632/78.) Body radioactivity was then measured in a whole body counter immediately after administration of the seleno bile acid and again 8 days later. Whole body retention of 75Se radioactivity after 8 days was only 0.15 percent of the originally administered dose as compared with a minimum of 13 percent for the ten normal humans after a similar elapse of time. Thus, tauro-23-[75Se]selena-25-homocholic acid affords a high level of discrimination between normal and ileal resected patients.

Comparative results obtained using 23-[75Se]selena-25-homodeoxycholic acid were 31% and 27% for normal patients and 7.5% for the ileal resected patient, a lower level of discrimination.

I claim:

1. A compound having the formula

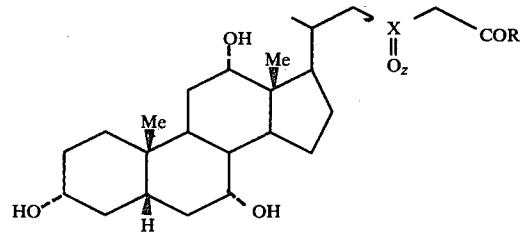

where
X is Se or Te,
z is 0 or 1, and
R is OH or a radical derived by removal of a hydrogen atom from the amino group of an amino acid.

2. A compound as claimed in claim 1 wherein X is 75Se.

3. A compound as claimed in claim 1 or claim 2, wherein z is 0.

4. A compound as claimed in claim 1 or claim 2, wherein R is OH or the radical derived from glycine or taurine.

5. The compound according to claim 1 which is 23-[75Se]selena-25-homocholic acid.

6. The compound according to claim 1 which is tauro-23-[75Se]selena-25-homocholic acid.

7. The compound according to claim 1 which is glyco-23-[75Se]selena-25-homocholic acid.

8. A compound as claimed in claim 3, wherein R is OH or the radical derived from glycine or taurine.

* * * * *